United States Patent
Siebert et al.

(10) Patent No.: US 6,368,625 B1
(45) Date of Patent: Apr. 9, 2002

(54) ORALLY DISINTEGRABLE TABLET FORMING A VISCOUS SLURRY

(75) Inventors: John M. Siebert, Eden Prairie; Rajendra K. Khankari, Maple Grove, both of MN (US); Unchalee Kositprapa, Davie, FL (US); S. Indiran Pather, Plymouth, MN (US)

(73) Assignee: Cima Labs Inc., Eden Prairie, MN (US)

( * ) Notice: Subject to any disclaimer, the term of this patent is extended or adjusted under 35 U.S.C. 154(b) by 0 days.

(21) Appl. No.: 09/372,738

(22) Filed: Aug. 11, 1999

Related U.S. Application Data

(60) Provisional application No. 60/096,265, filed on Aug. 12, 1998.

(51) Int. Cl.⁷ .............................. A61K 9/20; A61K 9/22; A61K 9/46
(52) U.S. Cl. ...................... 424/466; 424/464; 424/465; 424/468; 424/490; 514/770; 514/772.3; 514/777; 514/778; 514/781
(58) Field of Search .................. 424/464, 465, 424/466, 489, 435, 441, 439, 490, 468

(56) References Cited

U.S. PATENT DOCUMENTS

| | | |
|---|---|---|
| 3,011,950 A | 12/1961 | Mehaffey |
| 3,142,621 A | 7/1964 | Lazarus et al. |
| 3,456,049 A | 7/1969 | Hotko et al. |
| 3,885,027 A * | 5/1975 | Shaw et al. .................... 424/44 |
| 4,070,494 A | 1/1978 | Hoffmeister et al. |
| 4,414,198 A | 11/1983 | Michaelson |
| 4,454,110 A | 6/1984 | Caslaysk et al. |
| 4,610,870 A | 9/1986 | Jain et al. |
| 4,687,662 A * | 8/1987 | Schobel ........................ 424/44 |
| 4,695,467 A | 9/1987 | Uemura et al. ............. 424/502 |
| 4,710,384 A | 12/1987 | Rotman |
| 4,717,723 A | 1/1988 | Sugden |
| 4,883,660 A | 11/1989 | Blackman et al. |
| 4,950,689 A | 8/1990 | Yang et al. |
| 4,963,367 A | 10/1990 | Ecanow |
| 5,102,664 A | 4/1992 | Day |
| 5,133,974 A | 7/1992 | Paradissis et al. .......... 424/480 |
| 5,215,752 A | 6/1993 | Lovrecich et al. |
| 5,215,758 A | 6/1993 | Krishnamurthy |
| 5,273,823 A | 12/1993 | Hwang et al. |
| 5,288,497 A | 2/1994 | Stanley et al. |
| 5,288,500 A | 2/1994 | Ibsen |
| 5,318,780 A | 6/1994 | Viegas et al. |
| 5,368,862 A | 11/1994 | Colegrove |
| 5,419,918 A | 5/1995 | Lundberg |
| 5,422,122 A | 6/1995 | Powell |
| 5,462,749 A | 10/1995 | Rencher |
| 5,464,632 A | 11/1995 | Cousin et al. |
| 5,508,043 A | 4/1996 | Krishnamurthy |
| 5,529,777 A | 6/1996 | Andrianov et al. |
| 5,545,423 A | 8/1996 | Soon-Shiong et al. |
| 5,556,640 A | 9/1996 | Ito et al. |
| 5,558,880 A | 9/1996 | Gole et al. |
| 5,576,021 A | 11/1996 | Andoh et al. |
| 5,585,379 A | 12/1996 | Sintov et al. |
| 5,587,175 A | 12/1996 | Viegas et al. |
| 5,587,180 A | 12/1996 | Allen, Jr. et al. |
| 5,595,760 A | 1/1997 | Cherif-Cheikh |
| 5,648,093 A | 7/1997 | Gole et al. |
| 5,728,401 A * | 3/1998 | Ahmed et al. ............... 424/466 |

\* cited by examiner

Primary Examiner—James M. Spear
(74) Attorney, Agent, or Firm—Lerner, David, Littenberg, Krumholz & Mentlik, LLP

(57) ABSTRACT

A dosage form which rapidly disintegrates in the mouth and forms a viscous slurry of either microcapsules or a powder is described. The rapidly disintegrating dosage form is meant for direct oral administration by placing a tablet or capsule in the mouth of a patient. Upon disintegration, a viscosity of the resulting slurry increases so as to form an organoleptically pleasant viscous material which retards the spread of insoluble materials including the drug.

39 Claims, No Drawings

ORALLY DISINTEGRABLE TABLET FORMING A VISCOUS SLURRY

This application claims the benefit under 35 U.S.C. 119(e) of U.S. Provisional Application No. 60/096,265, filed on Aug. 12, 1998.

FIELD OF THE INVENTION

The invention relates to the fields of pharmacy and medicine and to orally disintegrable dosage forms for the delivery of sustained or extended release microcapsules and/or prompt release coated or non-coated drug particles.

BACKGROUND OF THE INVENTION

There are many formulations known for administering extended or sustained release forms of various medicines. A common method involves the administration of microencapsulated or otherwise coated drug substances. Coating can be errodable or disintegrable or it can be selectively porous, effectively controlling the release or diffusion of the drug contained within it. The administration of such particles is, not without complexity. Tableting may crush the particles interfering with their otherwise preplanned drug administration rate. Suspension or liquid vehicles may be desirable, but the potential for leakage of the drug is increased. Capsules containing granules or beads may be an alternative. However, each new coating stage adds additional complexity and can modify the overall release profile of the drug.

Indeed, this latter problem is common to tablets as well. While much care may be taken in ensuring that the microencapsulated drug will release at a certain rate, placing sufficient material into a hard tablet for ingestion can change the release profile. It will take some time for the body to sufficiently digest the tablet and allow it to decompose or disintegrate into its component parts thereby releasing the microcapsules or microparticles. This adds an additional variable to the release profile and complicates formulation significantly.

One method of addressing these complications is by the provision of in-mouth, rapidly disintegrable tablets. These tablets will disintegrate in the mouth and release the microcapsules or microparticles which can then be swallowed. In essence, the tablet is useful for conveying the microencapsulated materials to the body. However, it disintegrates sufficiently rapidly such that it will not become an impediment or a significant factor in the overall release profile. By the use of this technology, ideally the release rate and profile of the drug would be identical to that of a standard tablet which is ingested or to that of an equivalent amount of microparticles which are swallowed.

Nonetheless, there is considerable room for improvement. Sustained-release or extended-release microcapsules and microparticles tend to be relatively larger and are often relatively hard. If an in-mouth delivery system is used, these particles are then released into the mouth and produce a sandy or gritty feel. This feel is exacerbated by large quantities of microencapsulated materials and/or the inclusion of relatively larger, tactily more significant, particles. It is an aim of the invention to address this problem.

Other problems are encountered in the formulation of prompt release, orally disintegrable tablets, especially those containing taste masked drug substances. These problems include "local accumulation." Upon disintegration in the mouth, local accumulations of powder may occur which are not immediately swallowed. Powder may adhere to various parts of the oral cavity such as the tongue, mucus membranes and between the teeth. These local accumulations of powder may have an unpleasant mouth fee. Moreover, if the dosage form contains unpleasant tasting drug particles which are taste masked by means of coating, adherence in the oral cavity allows a greater opportunity for dissolution of the coating and, hence, release of the drug into the oral cavity. The dissolved drug diffuses through the saliva to reach the taste buds, resulting in the patient experiencing an unpleasant taste.

SUMMARY OF THE INVENTION

The present invention solves these problems by, in one aspect, providing an orally disintegrable tablet suitable for use in the delivery of sustained or extended release formulations of coated granules, coated particles or microcapsules.

Applicants have found that a method of addressing the distasteful sensation which may accompany the use of extended or sustained release coated formulations is by providing a material which will decompose or disintegrate in the mouth so as to form a relatively viscous slurry with saliva. This viscous saliva slurry will help contain the particles as a loose but cohesive mass thereby preventing the particles from distributing throughout the mouth, i.e., under the tongue, between the gums and lips, etc. This therefore provides a greatly enhanced organoleptic sensation. This is accomplished by providing an in-mouth disintegrable formulation (orally disintegrating tablets, capsules, etc.) that includes an in-mouth viscosity enhancer which provides a pleasant mouth feel and helps to cause the individual particles to associate with each other and with saliva to thereby incorporate the extended release particles into a salivary mass of increased viscosity. This in turn allows the particles to stay together and glide smoothly and be easily swallowed. This in-mouth viscosity enhancing material can be, for example, an in situ formed gel or a material such as gums or various polymers. Mixtures are also contemplated.

The tablet preferably contains between about 10 and about 80% of an extended release coated material by weight of the tablet. For convenience, we will refer herein to these coated materials as "microcapsules." However, it should be understood that this term contemplates the use of any extended, enteric or sustained-release vehicle, including microgranules, granules, microcapsules, particles, microparticles, adsorbates and the like known in the industry. Indeed, these particulate materials, referred to collectively herein as "microcapsules," need not necessarily be coated at all; so long as they can achieve an extended release. These microcapsules generally have a particle size ranging from between about 50 to about 3,000 microns and include between about 5 and about 70% of a coating based on the weight of the microcapsules. The coating is an extended or enteric release coating.

The tablet also generally includes between about 5 and about 60% of a rapidly dissolvable sugar or sugar alcohol filler. The rapidly dissolvable sugar or sugar alcohol filler has a particle size selected to be complementary to the particle size of the microcapsules and generally ranges between about 300 and about 1,500 microns. The tablet also includes between about 0 and about 35% of a binder, including insoluble filler-binders, between about 1 and about 40% of a disintegrant; and between about 0 and about 50% of an effervescent couple. The sugar or sugar alcohol, binder disintegrant and if present, the effervescent couple are all provided in amounts based on the weight of the finished tablet.

By the use of the present invention one can develop in-mouth disintegrable tablets which can disintegrate in the mouth in under a minute, preferably under 30 seconds. The thus disintegrated tablet releases the sustained or extended release microcapsules into the mouth. The use of the viscosity enhancer helps to maintain the available saliva, excipients and microparticles as an integral mass. However, the resulting slurry remains both easy and pleasurable to swallow.

The present invention therefore solves the problems facing the prior art. Even with relatively large microcapsules, it is possible to obtain a dosage form which can disintegrate rapidly in the mouth and yet results in a pleasant organoleptic mouth feel. Relatively large microcapsules can be released into the mouth without a significant amount of chewing which could break the microcapsules and/or alter their release profile. The microcapsules are bound together, in a loose confederation, which reduces this tendency to dissipate throughout the mouth of the patient causing irritation, discomfort, and an adverse organoleptic sensation. Ideally, the pharmoco-kinetic performance of the drug administered through this dosage form will not be in any way altered by a comparison of the direct administration of equal amounts of non-tableted extended release microcapsules. Again, these increased organoleptic properties, coupled with the convenience of rapid and in-mouth disintegration, greatly assists in assuring compliance.

In another aspect of the present invention, closely related to that just described, the present invention provides a slurry generated in the mouth of a patient following the placement of a dosage form in the patient's mouth to serve as a binding medium to hold certain non-extended release/non-enteric coated active ingredients together as a mass which can easily be swallowed. This decreases the opportunity for the particles or powders to stick to membranes or between teeth, leaving an unpleasant mouth feel and/or unpleasant taste. Moreover, to the extent that any coated or encapsulated drug was to permeate the coating, it would encounter a viscous salivary mixture through which the dissolved drug must diffuse in order to reach the taste buds. Since diffusion through the viscous medium is slow, little, if any, of the drug is tasted before it is swallowed. These various mechanisms improve the organoleptic properties of the medication. Of course, the use of both the extended release microcapsules and powders in a single dosage form are also contemplated. This would provide both an immediate release of drug and prolonged release as well.

It will be appreciated that the term "powder" as used herein contemplates both a true powder, as well as truly crystalline materials, microgranulated and granulated materials, agglomerates, adsorbates and the like. In addition, when these powders are coated, the coating contemplated is a rapid release coating—one which can assist in providing effective taste masking while providing minimal inference with the coated active ingredient's normal dissolution profile. Ideally these coatings will dissolve, disintegrate or become sufficiently porous to allow the full release and dissolution of the coated drug in a manner consistent with the administration of the same drug in a completely uncoated fashion. Certainly, the use of these "coated powders" should not alter the dissolution rates of the drug in the digestive tract by more than an hour and preferably by less than half an hour.

In this way, these powder materials are distinguished from "microcapsules" having extended, sustained, or enteric coatings as discussed herein. For convenience, these coated and uncoated species will be encompassed within the term "powder."

Furthermore, while the various aspects of the present invention will principally be described in terms of the use of microcapsules i.e., extended, enteric or sustained release species, the formulations described are applicable to both microcapsules and powders unless noted otherwise. Therefore, for example, in a particular formulation, an equivalent amount of a powder can be substituted for an equivalent amount of microcapsules. Of course, some adjustments may be necessary to account for the relative differences in the weight of the coatings used. However, the amount of uncoated drug should be equivalent in each case.

Another aspect of the present invention is the discovery of an interesting synergy which exists by the use of effervescent materials in combination with the dosage forms described herein. In addition to the normal role of effervescence in stimulating the mouth's production of saliva, speeding disintegration, the aiding in taste masking, the presence of effervescence in the dosage forms of the present invention actually enhances the overall performance of these dosage forms. It is believed that effervescence helps provide a driving force and a mixing action which increases the speed with which the viscosity of the resulting slurry is formed. The effervescence also is believed to help carry the slurry away from the dissolving and disintegrating surface of the tablet such that the viscous slurry does not completely encapsulate same and retard further disintegration. Not a great deal of effervescence is required to obtain these results although the organoleptic properties of the dosage forms can be significantly altered based on the amount of effervescent material present.

DETAILED DESCRIPTION OF THE PREFERRED EMBODIMENT

In accordance with the present invention, "orally disintegrable" means that the tablet will disintegrate substantially into its component parts (e.g. the powder, microcapsules and insoluble excipients, etc.) within three minutes, preferably within two minutes or less and more preferably within about one minute or less. For very large tablets, i.e., 2,500 mg or above, greater than three may be required. However, such extended disintegration time is contemplated in the phrase "substantially disintegrated." "Dissolvable" or "dissolution," in accordance with the present invention, refers to certain components of the tablet of the present invention which are substantially soluble in water and saliva. At least about 50% by weight of such ingredients will dissolve and preferably within about 90 seconds of a tablet being placed in a patient's mouth.

Microcapsules in accordance with the present invention, includes active ingredients which are in the form of coated particles, microparticles, microcapsules, granules, microgranules, adsorbates, etc. and are provided in an amount of between about 10 and about 80% based on the tablet's weight. This means that between 10 and 80% of the weight of the finished tablet is made up of microcapsules. More preferably, the amount of microcapsules ranges from between about 20–70% by weight.

These microcapsules should have a particle size ranging from between about 50 to about 3,000 microns, and more preferably between about 300 to about 2,000 microns.

Of these microcapsules, between about 5 to about 70% by weight of the microcapsules themselves is made up of the enteric, sustained release or extended release coating. Preferably, the amount of coating, by weight of the microcapsules, ranges from between about 10 to about 40% and more preferably from between about 10 to about 20%.

The coating in accordance with the present invention is an extended or enteric release coating. By extended or enteric release it is understood that while the microcapsules are rapidly dispersed in the mouth the active ingredients or drug itself is released from the microcapsules slowly or in a manner that alters its otherwise normal release profile. By the use of these coatings, the time necessary between doses of drug can be extended relative to the use of the same quantity of uncoated particles or microcapsules. Preferably the extended release coatings in accordance with the present invention will provide for a release of drug, with as uniform a rate as possible, over a period of time ranging from between about 4 to about 48 hours and more preferably from between about 4 to about 24 hours.

Preferred extended release coatings in accordance with the present invention include, for example, cellulose ethers, cellulose esters, polymethacrylates and copolymers, polyvinylacetate copolymers. Cellulose ethers include hydroxypropylmethyl cellulose, ethyl cellulose, hydroxypropyl cellulose and sodium carboxymethyl cellulose. Cellulose esters include hydroxypropylmethyl cellulose phthalate, cellulose-acetate phthalate, and hydroxypropylmethyl cellulose acetate succinate. Polymethacrylates include methacrylic acid/methyl methacrylate copolymers, methacrylic acid-methyl acrylate copolymers and dimethyl amino-methyl methacrylate copolymers. Polyvinyl acetate copolymers include vinylacetate/vinylpyrrolidone copolymers polyvinylacetate phthalate and polyvinylpyrrolidone. Enteric coatings include, without limitation, cellulose acetate phthalate, shellac, hydroxypropyl methylcellulose phthalate, polyvinyl acetate phthalate, and a family of polymers sold under the trademark EUDRAGIT®.

The active ingredient can include pharmaceutical ingredients, vitamins, minerals and dietary supplements. Pharmaceutical ingredients may include, without limitation, antacids, analgesics, anti-inflammatories, antipyretics antibiotics, antimicrobials, laxatives, anorexics, antihistamines, antiasthmatics, antidiuretics, anti-flatuents, antimigraine agents, biologicals (proteins, peptides, oligonueleotides, etc.) anti-spasmodics, sedatives, antihyperactives, antihypertensives, tranquilizers, decongestants, beta blockers and combinations thereof. Also encompassed by the terms "active ingredient(s)," "pharmaceutical ingredient(s)" and "active agents" are the drugs and pharmaceutically active ingredients described in Mantelle, U.S. Pat. No. 5,234,957, in columns 18 through 21. That text of Mantelle is hereby incorporated by reference.

As used in this disclosure, the term "vitamin" refers to trace organic substances that are required in the diet. For the purposes of the present invention, the term "vitamin(s)" includes, without limitation, thiamin, riboflavin, nicotinic acid, pantothenic acid, pyridoxine, biotin, folic acid, vitamin $B_{12}$, lipoic acid, ascorbic acid, vitamin A, vitamin D, vitamin E and vitamin K. Also included within the term "vitamin" are the coenzymes thereof. Coenzymes are specific chemical forms of vitamins. Coenzymes include thiamine pyrophosphates (TPP), flavin mononucleotide (FMM), flavin adenine dinucleotide (FAD), Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme $B_{12}$, lipoyllysine, 11-cis-retinal, and 1,25-dihydroxycholecalciferol. The term "vitamin(s)" also includes choline, carnitine, and alpha, beta, and gamma carotenes.

The term "mineral" refers to inorganic substances, metals, and the like required in the human diet. Thus, the term "mineral" as used herein includes, without limitation, calcium, (calcium carbonate), iron, zinc, selenium, copper, iodine, magnesium, phosphorus, chromium and the like, and mixtures thereof. The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

In general, the amount of active ingredient incorporated in each tablet or dosage form may be selected according to known principles of pharmacy. An effective amount of pharmaceutical ingredient is specifically contemplated. By the term "effective amount," it is understood that, with respect, to for example, pharmaceuticals, a "pharmaceutically effective amount" is contemplated. A "pharmaceutically effective amount" is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

The amount of active ingredient used can vary greatly. Of course, the size of the dosage form, the requirements of other ingredients, and the number of, for example, tablets which constitute a single dose will all impact the upper limit on the amount of pharmacologically active ingredient which can be used. However, generally, the active ingredient is provided in an amount of between greater than zero and about 80% by weight of the finished tablet and, more preferably, in a range of between greater than zero and about 60% by weight thereof. Put in other terms, the active ingredient can be included in an amount of between about 1 microgram to about 2 grams, and more preferably between about 0.01 and about 1000 milligrams per dosage form, i.e., per tablet.

Dosage forms in accordance with the present invention also includes between about 5 and about 60% of a rapidly dissolvable sugar or sugar alcohol filler. This amount is based on the weight of the finished tablet. More preferably, the amount of such filler will range from between about 10 to about 35% by weight based on the tablet.

Rapidly dissolvable sugar and sugar alcohol in accordance with the present invention include, for example, mannitol, lactose, sucrose, maltose, dextrose, sorbitol, xylitol, maltitol, lactitol, and maltodextrins. Mannitol and other similar compounds having a negative heat of solution are preferred because they provide a particularly pleasant sensation enhancing the organoleptic experience of taking the tablet of the present invention. Most preferably, the filler is sucrose, mannitol, xylitol, lactose and maltose. When used at all, preferably only rapidly water soluble filler materials should be used.

Where necessary, granulated materials are used such that the particle size of the filler is complementary to that of the particle size of the microcapsules. "Complementary" does not mean that the particle sizes need be exactly the same.

However, the greater the degree of similarity, the greater the homogeneity of the material. The greater homogeneity, in turn, results in much greater uniformity of disintegration and dissolution. The particle size of the filler should therefore range from between about 100 to about 2,800 and more preferably between about 150 to about 1,500 microns.

For tableting purposes, a binder is preferred. The binder should be present in an amount of between about 0 to about 35% by weight based on the weight of the tablet. Preferably, the binder will be present in an amount which is greater than zero and indeed, in an amount of between about 3 to about 15%. Water soluble binders are preferred. But generally, such binders are water insoluble. Therefore, the effort should be made to minimize the content of such binders as the higher the overall content of insoluble materials such as the coated active, the lower the overall organoleptic quality of the formulation. Certain binders such as a number of insoluble filler-binders including microcrystalline cellulose sold under the trade name "AVICEL" have additional advantageous properties that, despite their insolubility, make them nonetheless more desirable than other similar binders. A number of AVICEL formulations such as, for example, type PH113 available from FMC Corporation, Princeton, N.J. can act as a dry binder. However, when placed in an aqueous environment such as, in a patient's mouth, the binder can actually aid in the disintegration of the tablet. In addition, microcrystalline cellulose imparts an almost creamy mouth feel which helps offset the negative impact of its insolubility. The use of such binders therefore helps reduce the overall amount of disintegrant which needs be used. Other binders include alginic acid, sodium alginate, starch, modified starches and other water swellable binders. Methyl cellulose is also preferred. Note that certain binders can also be used and classified as disintegrants as is known in the industry.

Other disintegrants are also often desirable.

Disintegrants, such as crospovidone (cross-linked polyvinyl pyrrolidone (cross-linked "PVP")) are generally water insoluble. While they add to the rapid disintegration of the formulation, their inclusion can also add to the total content of insoluble ingredients making it more difficult to strike a balance between disintegration/dissolution speed and the resulting organoleptic sensation. Preferably, the amount of disintegrant will range from between greater than zero, i.e., about 1 to about 40% by weight based on the weight of the tablet and more preferably between about 3 to about 20%. Other disintegrants useful include sodium starch glycolate, croscarmallose sodium, microcrystalline cellulose and starch.

An effervescent couple is also preferred for use in accordance with the present invention. When present at all, it can be provided in a relatively small amount. The effervescent couple provides a number of advantages in the overall context of the present formulation. First, it aids in the disintegration of the tablet making it easier for the dissolvable constituents to dissolve and rapidly create a slurry. The presence of effervescence can also help stimulate the generation of saliva again facilitating disintegration, dissolution and the formation of an in-mouth slurry. Finally, many find the sensation of a mild amount of effervescence to be pleasing and this helps facilitate compliance by enhancing the organoleptic properties of the tablet.

The term effervescent couple(s) includes compounds which evolve gas. The preferred effervescent couples evolve gas by means of chemical reactions which take place upon exposure of the effervescent couple to water and/or to saliva in the mouth. The bubble or gas generating reaction is most often the result of the reaction of a soluble acid source and alkali metal carbonate or carbonate source. The reaction of these two general classes of compounds produces carbon dioxide gas upon contact with water included in saliva.

Such water activated materials should be kept in a generally anhydrous state with little or no absorbed moisture or in a stable hydrated form since exposure to water will prematurely disintegrate the tablet. The acid sources or acid may generally include food acids, acid anhydrides and acid salts. Food acids include citric acid, tartaric acid, malic acid, fumaric acid, adipic acid and succinic acids, etc. Because these acids are directly ingested, their overall solubility in water is less important than it would be if the effervescent tablet formulations of the present invention were intended to be dissolved in a glass of water. Acids, anhydrides and salts may be used. Salts may include sodium, dihydrogen phosphate, disodium dihydrogen pyrophosphate, acid citrate salts and sodium acid sulfite.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate.

The effervescent couple of the present invention is not always based upon a reaction which forms carbon dioxide. Reactants which evolve oxygen or other gases which are safe are also considered within the scope. Where the effervescent couple includes two mutually reactive components, such as an acid source and a carbonate source, it is preferred that both components react completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, in other embodiments of the present invention, the amount of either acid or carbonate source may exceed the amount of the other component. This may be useful to enhance taste and/or performance of a tablet containing an overage of either component. In this case, it is acceptable that the additional amount of either component may remain unreacted. It may be desirable to add an excess of one component in order that the excess may react with an in situ gel forming substance. An example of this is an excess of sodium bicarbonate to react with alginic acid to form a gel.

In general, the effervescent couple may be provided in an amount of between greater than zero to about 50% by weight of the tablet. More preferably, it will be provided in an amount of greater than zero to about 35%. It is preferred, however, that the effervescent couple be provided in an amount which is greater than zero. Indeed, while neither a binder nor an effervescent couple is required to provide acceptable performance, the use of at least one of a binder and/or effervescent couple is preferred. Most preferably, some amount of both are provided. An effervescent couple may not be needed when certain in-mouth viscosity enhancers are used. In other instances, the liberated gas in conjunction with the viscosity enhancer results in a slurry of the required viscosity.

The in-mouth viscosity enhancer or viscosity modifiers in accordance with the present invention can include gels, in-situ gel formers, gums and polymeric materials. The in-mouth viscosity enhancing material may include, for example, in-situ gel formers such as alginic acid and a complimentary soluble metal carbonate, a gum such as arabic, xanthan, guar, etc. and carbopolymers such as carbopols available from Croda, Inc., hydroxymethyl cellulose, hydroxypropyl cellulose, hydroxypropyl methyl cellulose, etc. Most preferred are methylcellulose, hydroxypropylmethyl cellulose, hydroxyethyl cellulose, carbolpol and silicon dioxide. These materials are provided in an amount which is sufficient to increase the viscosity of the slurry that results from the disintegration and dissolution of the various other components of the tablet in a patient's mouth. However, the amount of such in-mouth viscosity enhancing ingredients must be controlled to ensure that an organoleptically acceptable slurry results and that the increased viscosity does not too adversely affect either the in-mouth disintegration time or the organoleptic properties of the formulation.

The amount of these viscosity enhancers used to provide sufficient cohesion and form an organoleptically acceptable (i.e. one which is palatable and preferably pleasant) slurry will vary greatly depending upon a number of factors including the volume of medicine to be delivered, the type of patient (the viscosity may need to be different for children than for adults) the disintegration time and the specific type of viscosity enhancer used. The amount used will be that which provides an effective amount of viscosity to the slurry resulting from the disintegration of the dosage form, the dissolution of the saliva dissolvable species and the release of the insoluble species. Generally, the amount of viscosity enhancer will range from between about 1 and about 36% by weight and more preferably between about 2 and about 20%. In any event, sufficient viscosity enhancers should be used to provide effective viscosity enhancement. This means that the resulting viscosity of the slurry should range from between 25,000 to 500,000 (centipoise) CPS and more preferably between about 25,000 and about 300,000 CPS.

A lesser amount of a gum, for example, may be necessary than the amount of components necessary for the in-situ formation of a gel. It may also be necessary to include the varying proportions of viscosity modifiers. Thus, for example, if an alginic acid based gel is desirable, a greater proportion of a soluble metal carbonate may be necessary as compared to the amount of alginic acid provided. Between about 1 to about 35% by weight of the tablet may be alginic acid and a stoichiometric amount, or an excess, of a carbonate radical precursor may be desirable.

The metal carbonate is, preferably, a carbonate or bicarbonate of an alkali or alkaline earth metal, such as the metal sodium, potassium, calcium, magnesium or manganese. While aliginic acid is specifically mentioned, other in-situ gel forming acids may also be used so long as gel formation can be rapid, sufficient viscosity can be achieved and both the precursor and the resulting gel is pharmaceutically acceptable. See U.S. Pat. No. 4,414,198 which is hereby incorporated by reference and also a copy of which is attached. The slurry that results from the disintegration of the dosage form and exposure of the in-mouth viscosity enhancer to saliva should begin to provide sufficient viscosity to result in cohesion and an acceptable organoleptic sensation within about a minute or less of placing the dosage form in a patient's mouth.

It will be appreciated that the disintegration of the dosage form, dissolution of selected excipients and formation of a viscous slurry does not necessarily happen all at once. As a tablet is placed in the mouth, its outer layer is exposed to saliva. AS the dissolvable materials dissolve and the tablet begins to disintegrate, microcapsules and/or powders are released and the viscosity enhancer begins to exert its influence helping mitigate the spread of the released drug and insoluble ingredients throughout the mouth. If a patient were to swallow while retaining the remainder of the dissolving tablet in their mouth, a more cohesive mass of material will be swallowed while the tablet continues its progression towards complete disintegration. Of course, the tablet material can be held completely in the mouth, without swallowing, in which case a more complete integral mass may eventually be swallowed. As each successive surface portion of the tablet is exposed to saliva, the available pool of viscous material is increased unless carried to another part of the mouth or swallowed.

This process can be greatly assisted by the presence of an effervescent material. The liberating gas helps to "stir things up" assisting in the stimulation of saliva necessary for the viscosity enhancers to be effective. They also help insure proper mixing of the viscosity enhancer with the saliva and other ingredients shortening the time necessary for the viscosity enhancing material to exert its influence.

Other common excipients such as, tableting lubricants, colors, sweeteners, flavors and the like may also be included. Lubricants, such as magnesium stearate should also be included in an amount of less than about 5% by weight of the finished tablet, preferably less than about 2% and most preferably about 0.5% by weight. The same is true for other excipients.

As previously noted, an equivalent amount of powder may be used in place of microcapsules. If the powder used is uncoated, then the amount of powder utilized is equal to the amount of active ingredient in encapsulated form used in the formulation as previously described. Therefore, if a tablet was to contain 70% coated acetaminophen and the acetaminophen was to be coated with an extended release coating that made up 20% by weight of the total weight of the microcapsule, then the amount of acetaminophen powder used would be equal to the amount of acetaminophen exclusive of the coating. In this example, the resulting amount of powder will make up a smaller percentage by weight of the total formulation, although the amount of acetaminophen administered in each instance is about the same.

If the acetaminophen powder was coated for taste masking purposes, then the amount of powder substituted for microcapsules in the formulation would also fall within the ranges previously described with a certain percentage of the powder being coating material as described herein. Any coating useful for taste masking, without significantly affecting the drug's dissolution properties may be used. Preferred coatings include Opadry (Colorcon), Surelease (Colorcon), Aquacoat (FMC) and Eudragit (Rohm). Combinations and multiple layers such as a coating of Eudragit E100 is used in one layer and Surelease and Opadry are mixed to form a second layer are also contemplated.

Tablets according to the present invention can be manufactured by well-known tableting procedures. In common tableting processes, material which is to be tableted is deposited into a cavity, and one or more punch members are then advanced into the cavity and brought into intimate contact with the material to be pressed, whereupon compressive force is applied. The material is thus forced into conformity with the shape of the punches and the cavity. Hundreds, and even thousands, of tablets per minute can be produced in this fashion. Various tableting methods, well known to those skilled in the art, are comprehensively discussed throughout *Pharmaceutical Dosage Forms: Tablets,* Second Edition, edited by Herbert A. Lieberman et al., Copyright 1989 by Marcel Dekker, Inc., incorporated by reference herein, as well as other well known texts. Tablets should be compressed to a hardness of between about 10 and about 50 Newtons and preferably, about 15 to about 40 Newtons.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

EXAMPLE 1

A coated powder formulation of Famotidine may be prepared as follows:

| Ingredients | Amount (g) |
| --- | --- |
| Famotidine | 500 |
| Surelease (Ethyl cellulose) | 1600 |
| Water | 1633.33 |
| Opadry (Hydroxypropyl methyl cellulose) | 100 |

A coating solution is prepared by initially stirring Opadry in water for about 30 minutes. Then, Surelease is added to the solution and stirred further. The coating of the Famotidine is then carried out as follows. Famotidine, screened through 20 mesh, is taken for coating. The airflow during the coating is maintained at 55 CMH (cubic meters/hr) and spray rate is 21 g/min. As coating proceeds, bed volume increases and hence, the airflow also increases to about 80 CMH. The inlet air temperature is maintained at about 80 C. to obtain a bed temperature of 39–41 C.

Tablets can be prepared from the following formulation (Tablet Size—⅜" Tablet Weight 300 mg):

| Ingredients | mg/300 mg tablet | % w/w per tablet |
| --- | --- | --- |
| Coated Famotidine | 40.00 | 13.3 |
| Mannitol | 151.10 | 50.4 |
| Aspartame | 15.00 | 5.0 |
| Sodium Bicarbonate | 9.00 | 3.0 |
| Citric Acid | 6.00 | 2.0 |
| Hydroxypropyl methly cellulose (K15M) | 30.00 | 10.0 |
| Microcrystalline cellulose (Avicel) | 30.00 | 10.0 |
| Silicon dioxide | 0.90 | 0.3 |
| Crospovidone, USP | 15.00 | 5.0 |
| Magnesium Stearate, NF | 3.00 | 1.0 |
| TOTAL | 300.00 | 100.0 |

Procedure: Weigh and screen all materials except Magnesium Stearate and blend for 30 minutes in a blender. Then, weigh and screen Magnesium Stearate and add to above blend and mix a further 5 minutes. The powder is discharged and tableted at about 15–20 Newtons.

EXAMPLE 2

A dosage form including microencapsules of Pseudoephedrine Hydrochloride may be prepared as follows:

| Ingredients | Amount (g) |
| --- | --- |
| LAYERING SOLUTION FORMULA | |
| Pseudoephedrine Hydrochloride | 600 |
| Hydroxypropyl methyl cellulose(E3 Prem LV11) | 11.86 |
| Polyethylene glycol 3350 | 1.19 |
| Purified water | 375.02 |
| COATING SOLUTION FORMULA | |
| Hydroxypropylmethylcellulose phthalate (HP-50) | 232.5 |
| Triethyl citrate | 17.5 |
| Ethanol | 1125 |
| Acetone | 1125 |

The layering solution is sprayed onto inert sugar beads (Nu-core white beads) at a rate of 36 g/min to obtain a weight gain of 200%. The airflow during the process is maintained between 60 and 48 CMH and the inlet air temperature is maintained at 65 C. After layering, the beads are screened through a 30 mesh screen.

The coating solution is then sprayed onto the layered beads where the airflow is maintained at 60 CMH, and the spray rate is 21 g/min. The inlet air temperature is maintained at 85 C. Coating is carried out to obtain a weight gain of 26%. These coated beads may then be tableted as described in the tableting procedure above.

The microcapsules are then tableted as follows (Tablet Size—⅝"Tablet Weight—700 mg):

| Ingredients | mg/700 mg tablet | % w/w per tablet |
| --- | --- | --- |
| Coated beads | 161.00 | 23.0 |
| Mannitol | 159.60 | 22.8 |
| Prosolv 90 (silicified microcrystalline cellulose) | 20.30 | 2.9 |
| Sodium Bicarbonate | 84.00 | 12.0 |
| Citric Acid | 56.00 | 8.0 |
| Hydroxypropyl methyl cellulose (K15M) | 175.00 | 25.0 |
| Silicon dioxide | 2.10 | 0.3 |
| Crospovidone, USP | 35.00 | 5.0 |
| Magnesium Stearate, NF | 7.00 | 1.0 |
| TOTAL | 700.00 | 100.0 |

Procedure: Weigh and screen all materials except Magnesium Stearate and blend for 30 minutes in a blender. Then, weigh and screen Magnesium Stearate and add to above blend and mix a further 5 minutes. The tablets are then compressed with this blend at about 15–20 Newtons. However, tablets can be compressed at from between 15–50 Newtons.

We claim:

1. A dosage form which disintegrates in the mouth of a patient comprising: at least one active ingredient in the form of a powder or microcapsule and in an amount which is sufficient to elicit therapeutic response; a filler; and at least one in-mouth viscosity enhancing material in an amount which is effective to provide an organoleptically acceptable viscous slurry having a viscosity range from between about 25,000 and about 500,000 CPS upon the disintegration of the dosage form in a patients mouth.

2. The dosage form of claim 1, wherein the microcapsule comprises an enteric, sustained release or extended release coating.

3. The dosage form of claim 1 wherein the viscosity of said organoleptically acceptable slurry ranges from between about 25,000 and about 300,000 CPS.

4. The dosage form of claim 1 wherein said in-mouth viscosity enhancing material is provided in an amount of about 1 to about 36% by weight based on the weight of the finished dosage form.

5. The dosage form of claim 4 wherein said in-mouth viscosity enhancing material is provided in an amount of about 2 to about 20% by weight based on the weight of the finished dosage form.

6. The dosage form of claim 1 wherein said in-mouth viscosity enhancing material is provided in an amount of about 1 to about 36% by weight based on the weight of the finished dosage form.

7. The dosage form of claim 1 wherein said active ingredient is provided in an amount of between about 1 microgram and about 2 grams based on the weight of uncoated drug.

8. The dosage form of claim 7 wherein said active ingredient is provided in an amount of between about 0.01 and about 1000 milligrams based on the weight of uncoated drug.

9. The dosage forms of claim 1 wherein said filler is a rapidly dissolvable sugar or sugar alcohol.

10. The dosage form of claim 9 wherein said filler is provided in an amount of between about 5 and about 60% by weight based on the weight of the finished dosage form.

11. The dosage form of claim 10 wherein said filler is provided in an amount of between about 10 and about 35% by weight based on the weight of the finished dosage form.

12. The dosage form of claim 1 further comprising at least one binder.

13. The dosage form of claim 12 wherein said binder is present in an amount of between about greater than zero and about 35% by weight based on the weight of the finished dosage form.

14. The dosage form of claim 13 wherein said binder is present in an amount of between about 3 and about 15% by weight based on the weight of the finished dosage form.

15. The dosage form of claim 12 wherein said binder is water soluble.

16. The dosage form of claim 1 further comprising at least one disintegrant.

17. The dosage form of claim 16 wherein said disintegrant is present in an amount of between about greater than zero and about 40% by weight based on the weight of the finished dosage form.

18. The dosage form of claim 13 wherein said disintegrant is present in an amount of between about 3 and about 20% by weight based on the weight of the finished dosage form.

19. The dosage form of claim 12 wherein said disintegrant is water soluble.

20. The dosage form of claim 1 further comprising at least one effervescent couple.

21. The dosage form of claim 16 wherein said effervescent couple is present in an amount of between about greater than zero and about 50% by weight based on the weight of the finished dosage form.

22. The dosage form of claim 13 wherein said disintegrant is present in an amount of between about greater than zero and about 35% by weight based on the weight of the finished dosage form.

23. A dosage form which disintegrates in the mouth of a patient comprising: at least one active ingredient in the form of a powder or microcapsule and in an amount which is sufficient to elicit therapeutic response; a filler; and at least one in-mouth viscosity enhancing material in an amount which is effective to provide an organoleptically acceptable viscous slurry having a viscosity range from between about 25,000 and about 500,000 CPS upon the disintegration of the dosage form in a patients mouth and at least one effervescent couple.

24. The dosage form of claim 23 wherein said effervescent couple is present in an amount of between about greater than zero and about 50% by weight based on the weight of the finished dosage form.

25. The dosage form of claim 24 wherein said effervescent couple is present in an amount of between about greater than zero and about 35% by weight based on the weight of the finished dosage form.

26. The dosage form of claim 2, wherein the microcapsule comprises an extended release coating and wherein said extended release coating comprises cellulose ethers, cellulose esters, polymethacrylates and copolymers, polyvinyl acetate copolymer.

27. The dosage form of claim 25 wherein the viscosity of said organoleptically acceptable slurry ranges from between about 25,000 and about 300,000 CPS.

28. The dosage form of claim 23 wherein said in-mouth viscosity enhancing material is provided in an amount of about 1 to about 36% by weight based on the weight of the finished dosage form.

29. The dosage form of claim 28 wherein said in-mouth viscosity enhancing material is provided in an amount of about 2 to about 20% by weight based on the weight of the finished dosage form.

30. The dosage form of claim 23 wherein said active ingredient is provided in an amount of between about 1 microgram and about 2 grams based on the weight of uncoated drug.

31. The dosage form of claim 30 wherein said active ingredient is provided in an amount of between about 0.01 and about 1000 milligrams based on the weight of uncoated drug.

32. An orally disintegrable tablet suitable for use in the delivery of at least one active ingredient in the form of microcapsules or powders comprising: between about 10 and about 80% of active ingredient containing microcapsules or powders by weight based on the weight of the tablet, said microcapsules or powder having a particle size ranging from between about 50 to about 3,000 microns, an amount of at least one in-mouth viscosity enhancer, which is sufficient to provide a viscous, swallowable, organoleptically acceptable mass containing said microcapsules, within about 3 minutes when placed in a patients mouth, said in-mouth viscosity enhancer being selected from the group consisting of methylcellulose, hydroxypropylmethyl cellulose, hydroxyethyl cellulose, carbopol and silicon dioxide; optionally between 0 and about 60% of a rapidly dissolvable sugar or sugar alcohol filler by weight of the tablet selected from the group consisting of sucrose, mannitol, xylitol, lactose and maltose; optionally between 0 and about 35% of a binder by weight of the tablet selected from the group consisting of microcrystalline cellulose and methyl cellulose; optionally between 0 and about 40% of a disintegrant by weight based on the weight of the tablet selected from the group consisting of sodium starch glycolate and crospovidone; and optionally between 0 and about 50% of an effervescent couple based on the weight of the tablet wherein said effervescent couple is present and is present in an amount of between about greater than zero and about 50% by weight based on the weight of the finished dosage form.

33. The dosage form of claim 32 wherein said effervescent couple is present in an amount of between about greater than zero and about 35% by weight based on the weight of the finished dosage form.

34. The dosage form of claim 32 wherein the viscosity of said organoleptically acceptable slurry ranges from between about 25,000 and about 500,000 CPS.

35. The dosage form of claim 34 wherein the viscosity of said organoleptically acceptable slurry ranges from between about 25,000 and about 300,000 CPS.

36. The dosage form of claim 32 wherein said in-mouth viscosity enhancing material is provided in an amount of about 1 to about 36% by weight based on the weight of the finished dosage form.

37. The dosage form of claim 36 wherein said in-mouth viscosity enhancing material is provided in an amount of about 2 to about 20% by weight based on the weight of the finished dosage form.

38. The dosage form of claim 32 wherein said active ingredient is provided in an amount of between about 1 microgram and about 2 grams based on the weight of uncoated drug.

39. The dosage form of claim 38 wherein said active ingredient is provided in an amount of between about 0.01 and about 1000 milligrams based on the weight of uncoated drug.

* * * * *

UNITED STATES PATENT AND TRADEMARK OFFICE
CERTIFICATE OF CORRECTION

PATENT NO.    : 6,368,625 B1
DATED         : April 9, 2002
INVENTOR(S)   : John M. Siebert, Rajendra K. Khankari, Unchalee Kositprapa, and S. Indiran Pather It is certified that error appears in the above-identified patent and that said Letters Patent is hereby corrected as shown below:

<u>Column 12,</u>
Line 62, change 'patients" to -- patient's --;

<u>Column 13,</u>
Line 21, change "forms" to -- form --;

<u>Column 14,</u>
Line 2, change "patients" to -- patient's --;
Line 46, change "patients" to -- patient's --;

Signed and Sealed this

Twenty-third Day of July, 2002

*Attest:*

JAMES E. ROGAN
*Attesting Officer*          *Director of the United States Patent and Trademark Office*